United States Patent [19]

Comi et al.

[11] Patent Number: 4,471,053

[45] Date of Patent: Sep. 11, 1984

[54] PROCESS FOR PRODUCING A VASAL FIBRINOLYTIC ACTIVE PRINCIPLE AND THE ENZYMATIC PRODUCT SO PREPARED

[75] Inventors: Gaetano Comi; Maurizio Pandolfi, both of Florence, Italy

[73] Assignee: Societa Italo-Britannica L. Manetti-H. Roberts & C., Florence, Italy

[21] Appl. No.: 366,276

[22] Filed: Apr. 7, 1982

[30] Foreign Application Priority Data

Apr. 23, 1981 [IT] Italy ............................... 48332 A/81

[51] Int. Cl.³ .......................... C12N 9/64; C12N 9/48
[52] U.S. Cl. ..................................... 435/226; 435/212
[58] Field of Search ............... 435/212, 215, 216, 217, 435/218, 226

[56] References Cited

U.S. PATENT DOCUMENTS

| 3,998,847 | 12/1976 | Reich et al. | 260/340.5 |
| 4,245,051 | 1/1981 | Eder et al. | 435/212 |
| 4,374,830 | 2/1983 | Schneider | 435/212 X |
| 4,381,346 | 4/1983 | Husain et al. | 435/215 |

*Primary Examiner*—Lionel M. Shapiro
*Attorney, Agent, or Firm*—Ladas & Parry

[57] ABSTRACT

A natural active principle enzymatic in type, called angiokinase, is obtained with an extraction procedure starting from mammalian connective tissue, such as from cattle and the like. The active principle comprises a new drug for the prophylaxis and treatment of all symptoms of abnormal fibrin formation and thrombus formation in various sites and localizations, such as atherosclerotic diseases and diabetic retinopathy, as well as thrombosis and thromboembolisms.

19 Claims, 6 Drawing Figures

PROCESS FOR PRODUCING A VASAL FIBRINOLYTIC ACTIVE PRINCIPLE AND THE ENZYMATIC PRODUCT SO PREPARED

The present invention refers to an extraction process for the production of a vasal fibrinolytic active principle starting from mammalian connective tissue, as well as to the specific enzymatic product so obtained, called 'angiokinase.' The invention moreover relates to the use of said product in pharmaceutical formulations for the prevention and treatment of diseases caused by abnormal fibrin and thrombus formation in various sites and localizations.

Background of the Invention

The principle object of this invention is to provide a new natural extractive principle, enzymatic in type, with fibrinolytic action in vivo, both direct and through plasminogen activation. Since said principle is obtained from the highly vascularized connective tissue of meat animals, it may be named simply and unequivocally 'angiokinase' in analogy with urokinase, the proteolytic plasminogen-plasmin activator isolated from the urine of male human subjects (see U.S. Pat. Nos. 2,961,382; 2,983,647; 2,989,440; 3,081,236; see also White et al., *Biochemistry*, 5, 2160, 1966). Another analogous name is 'streptokinase,' another plasminogen activator isolated from hemolytic streptococcus cultures (see U.S. Pat. Nos. 3,016,337; 3,042,586; 3,063,913; 3,063,914; 3,107,203; 3,138,542; 3,276,304).

The significance and the precise meaning of this invention, as well as the utility of its application to the prevention and cure of venal and arterial thrombosis in human subjects will be more readily appreciated after a brief discussion of the currently accepted and widely known view that mammalian blood vessel walls show fibrinolytic action. Said action involves the production of principles specific to this activity, currently known as plasminogen activators. Early views were that the fibrinolytic activity of the vasal wall would predominantly involve the veins and small vessels, but later the activity was observed in large vessels as well, in particular in the wall of the aorta. Research has shown that the blood vessel walls in human subjects killed in accidents (after incanulation of the femoral artery and vein) contained a considerable quantity of so-called 'plasminogen activators.'

There was no effective conclusion to the above studies regarding the isolation by chemico-physical extraction of a particular active principle from the vasal wall and from other highly vascularized connective tissues. Therefore, the present invention proposes the isolation and characterization of the active fibrinolytic principle from blood vessels in general and from the aorta in particular, called angiokinase, previously unknown. The invention also relates to its clinical use for therapeutic indications as a general antithrombotic and also within certain limits as a platelet anti-aggregant. In fact, the presence of angiokinase due to the onset of fibrinolytic activity on the part of the walls and then the blood, provides a first level of resistance to thrombosis conditions in warm blooded animals, including humans.

Thus the substance angiokinase, isolated and described in this invention, is the fibrinolytic principle in vasal walls in general and in the aorta in particular, which may be re-added to circulating blood to provide said blood with fibrinolytic potential.

Angiokinase shows the important property that it acts both as an activator (plasminogen plasmin) and as an actual plasmin. This finding is well documented, as described below in support of the invention, and is of considerable theoretical as well as practical significance. Up until now, all studies of the fibrinolytic activity of vasal walls have only revealed the simple activation effects of the pre-formed plasminogen in circulation. Angiokinase however also acts directly in exactly the same way as plasmin.

The areas of use of the present invention will be discussed in detail below.

As is well known, an event of particular importance in circulating pathology, at both venal and arterial levels, is the endovasal deposit of fibrin—said event leads both to stenosis of the vasal lumen and to occlusion (thrombosis).

Fibrin deposition also plays a particularly important role in white platelet thrombus formation, since it is required for adhesion of the platelets to the vasal wall and for platelet aggregation as well as for stabilization of the platelet aggregate.

Keeping the interface between blood and vasal wall free is an important and fundamental process in physiopathology.

It is also well known that the endovasal occlusive event (stenosis and thrombosis) is an indispensable and determining factor for a clinically non-detectable blood vessel condition to become visible on the symptomatic level and to thus become a clinically manifest disease.

This is quite freqnently the case in the athero-arteriosclerotic process which in itself is clinically invisible but becomes evident on the clinical level only (or mainly) when the endovasal stenosis process is accentuated or superceded by actual occlusion.

Therefore, for both prevention and therapy, it is of prime importance to on the one hand block and prevent the formation and accentuation of fibrin deposits and on the other to dissolve these deposits after they are formed.

As is well known, to this end therapy must be instituted to dissolve the fibrin which is forming and the fibrin deposits already formed.

This therapy thus involves the known products with fibrinolytic activity.

The medical profession is in complete agreement regarding the significance and importance of fibrinolytic therapy: it assumes a primary role in circulatory pathology.

There are two conditions underlying fibrinolytic therapy; The first is that, as mentioned above, fibrin is a determining factor in stenosis and endovasal occlusion.

The second is that a deficit in fibrinolytic activity in the blood-vascular system is a pathogenetic factor of prime importance not only in conditioning for the stenosis and vasal occlusion process but also in the same conditioning for atherosclerotic disease.

Too little capacity in the production or release of fibrinolytic activity by the vasal wall is an important factor in determining the atherosclerotic process in general and the endovasal occlusive process in particular. Therefore, a deficit in blood-vasal fibrinolytic capacity has considerable importance for the apthogenesis of atherosclerotic disease as well as for determining its most severe complication—thrombosis.

It is also well known that tissues rich in blood vessels, arterial and venous, are able to produce and release plasminogen activators and thus to show fibrinolytic activity. This then is a tissue activator of plasminogen, meaning the production of fibrinolytic activator at both tissue and vasal levels.

Using the methods of tissue extraction, histo-chemistry and in vitro tissue cultures, tissue and vascular fibrinolytic activity has been demonstrated and widely confirmed, and even measured at natural levels. It is known that tissue activators can be isolated from the heart, lung, ovary, prostate, uterus, etc.: these tissue activators are currently known as TA.

The plasminogen activator, which plays the most important role in intravascular fibrinolysis, is thought to be that synthesized by the endothelial cells topping the blood vessels. Since this enzyme has not yet been isolated and characterized, it has not yet been possible to identify this vascular activity with that of the tissue activator, even though these activities may really be the same.

The vascular or endothelial activator has been the object of numerous studies, and has been recognized and demonstrated, as well as even isolated, from the experimental medicine and biological activity points of view. The plasminogen activator has even been isolated and demonstrated from the vascular tissues of human cadavers.

However, it should be noted that during the thrombotic event, both arterial and venous, the capacity for fibrinolytic production is in deficit and compromised.

Another significant fact to be considered is the reason why this is held to be very important not only for the thrombotic complications arising during the course of ongoing vasculopathies (for example, athero-arteriosclerotic and varicose complications) but also for their pathogenesis, as already mentioned for the presence of a fibrinolytic deficit of the vasal wall.

The lack of plasminogen activators characterized atherosclerotic disease.

A significant correlation has been noted between reduced fibrinolytic activity by the arterial wall and susceptibility to atherosclerosis. A deficiency in this activity has been found to be directly proportional to greater and more severe susceptibility and sensitivity to experimentally-induced atheromatous processes.

Moreover, administration of antifibrinolytic agents aggravates the atheromatous process, while administration of fibrinolytic agents attenuates it.

Likewise, administration of antifibrinolytic drugs increases the risk of thrombotic complication, and the risk of systemic thrombotic complications must be taken into account when antifibrinolytic drugs are administered.

On a clinical level, a deficit of fibrinolytic activity has also been shown in atherosclerotic disease, which could be related mainly to a deficit in the production and release of plasminogen activators by the vasal wall and its endothelium in particular.

In atherosclerotic vascular conditions, a real incapacity and reduced power of fibrinolytic response by the vasal wall has been found.

Another particularly important finding has been a deficit of local fibrinolytic activity, or rather of a deficit predominantly corresponding to the vascular regions affected by the atherosclerotic process as compared to less affected and undamaged areas.

With regard to the human myocardium after suffering an infarction (extracts from myocardial tissue soon after an infarction), a sharp reduction of absence of fibrinolytic activity has been found. However, myocardial tissue extracts from infarcted areas in the fibrosis and connective repair phase show said activity.

Analogous results were found in experimentally-induced myocardial infarction: the fibrinolytic activity previously lacking was then found in lesioned areas undergoing repair, because of the plasminogen activators in the newly formed blood vessels.

Another significant finding is that of a fibrinolytic compromission in occlusive venal conditions. Fibrinolytic activity is reduced and compromised in the wall of the thrombus-affected vein. Low fibrinolytic activity in the vasal wall was found to be associated with an increased tendency to develop thrombosis in the deep veins. Thus a large percentage of a large series of patients with severe thromboembolic disease showed decreased fibrinolytic activity of the vasal wall.

The correlation between low fibrinolytic activity of the vasal wall and the blood on the one hand and the onset of thrombosis or pre-thrombotic conditions on the other has been confirmed in several studies.

Diabetes melitis, especially in combination with obesity, has been associated with reduced vascular and/or blood fibrinolysis due to stasis.

It is also known that obesity increases the predisposition of diabetics to vascular occlusions.

With regard to another situation favouring thrombosis development, depressed fibrinolytic activity in the venal wall, and/or reduced release of fibrinolysis activators be the vascular wall, has been found to be a regular post-operatory phenomenon, one that is particularly depressed in those patients who developed thrombosis.

Also, immediately after serious operations, the vascular endothelium cannot respond to stasis as it could before the operation. The term 'endothelial decompensation' has been suggested to explain the decrease in fibrinolytic activation in the post-operatory period.

Reduced tissue fibrinolysis is thought to be implicated in post-thrombotic syndrome, with consequent insufficient blood supply to the skin and ulceration.

These clinical and experimental data show that parietal plasminogen activator is greatly decreased in thrombinogenesis, and this observation suggests that these agents are consumed in the attempt to resolve the thrombosis.

Further evidence for the antithrombotic action of the vascular plasminogen activator was obtained when it was found that the greatest danger of experimentally-induced occlusion (for example, during the first eleven days after an operation) generally coincided with reduced or even absent fibrinolytic activity by the vascular wall.

All of the known data in this field have convinced experts in the area that adequate fibrinolytic treatment is an important part of human therapy in the indicated cases.

Description of the Prior Art

The area of the present invention, in relation to the improvement it affords over previous techniques, may be described in the following general terms.

Currently available fibrinolytic activators are well known to be of the indirect or direct types.

(a) Indirect means

These are not part of the actual fibrinolytic system, but rather stimulate the tissues (for example, vasal wall) to produce fibrinolytic activators (for example, stanazolol, ethyl estrenol, penphormin) or can mobilize the already produced activators from the wall (for example, nicotinic acid and its derivatives, acetylcholine, etc.).

The former show more continuous fibrinolytic activity which is however rather modest and somewhat slow—sometimes months of treatment are needed before any effects are seen.

The latter show more rapid and pronounced action, which however is completely transitory and followed by periods of reduced fibrinolytic activity during which the organism is more susceptible to thrombosis.

(b) Direct means

These form part of the fibrinolytic system itself, and involve both STK (streptokinase) and UK (urokinase) mentioned above. These are in effect the agents almost always used.

It must be noted that while these agents can develop prompt and continuous fibrinolytic activation, they are still far from satisfying physiopathological and clinical requirements. In particular, STK suffers the handicap of antibody inactivation. Moreover, both STK and UK provide fibirnolytic activation which leads to plasmin formation, which is in turn inactivated by antiplasmins.

In fact, the fibrinolytic activation induced by STK and UK, and thus the consequent plasmin formation (the essential condition for their effective action), runs counter to the inhibition caused by the antiplasmins in circulation and in particular by the fast-acting $alpha_2$ antiplasmin. This fact leads to the neutralization of a given part of these activators, and so necessarily to the use of elevated dosages to overcome this inhibition, with consequent risk of hemorrhage.

Moreover, UK differs from the tissue activator and thus from the vascular plasminogen activator in that it forms part of the fibrin-free urinary system and is thus extraneous to the blood vessel regions. Therefore, UK shows low affinity for fibrin, unlike the vascular plasminogen activator with its fairly pronounced activity in this regard. Synthesized by the kidney and isolated from the urine, UK is localized in the urinary tract where it has no effect on intravascular fibrinolysis.

Object of the Invention

The object of the present invention is a process the isolation and preparation in therapeutically suitable form, and a tissue plasminogen activator obtained via an extraction process from richly vascularized mammal organs and tissues.

Given its enzyme-type activity, said activator has been named 'angiokinase' in analogy with urokinase and streptokinase.

The tissue plasminogen activator, including that from the vasal wall (also known as 'endothelial activator' since it is produced by the vascular endothelia), differs from urokinase and streptokinase in its affinity for fibrin. This phenomenon was used in its isolation, as described below.

Endothelial plasminogen activator is readily adsorbed by the fibrin surface, facilitating plasminogen activation in this site. The plasminogen activator present in the blood is very probably identical to the vasculatar plasminogen activator that is object of the invention. In turn, the plasminogen activators in the tissues are probably very similar or identical to the blood and vascular activator.

Prior to this invention, the tissue activator (endothelial) has not been available for therapy even though it was hypothesized to be the most effective.

Vascular plasminogen activator is tightly adsorbed by the fibrin. The fibrin site which fixes the plasminogen is the same as that which fixes the vascular activator. In this way, a single mixture is formed of plasminogen, its activator and the fibrin to form plasmin on the inside of the thrombus.

In this way, the plasmin site which fixes it is rapidly occupied by the fibrin, to then protect the plasmin from inhibition by $alpha_2$ antiplasmin. STK and UK, however, as mentioned above, are subject to antiplasmin inhibition.

It is thus obviously quite important to have available for therapy the correct form of the tissue plasminogen activator according to this invention, in particular the vascular or endothelial activator.

The active fibrinolytic principle according to this invention was previously known only in the limited terms of its supposed existence based on its biological effects. It was called angiokinase since it comes from the vasal wall, or in any case from rich vascularized tissues.

Its undoubted biological activity has been confirmed based on a mechanism of action particularly suited to its physiopathological and therapeutic ends.

The active principle of this invention offers the following advantages over current practice, i.e., the use of STK and UK:

1. Precise, rapid and significant fibrinolytic activity.
2. This fibrinolytic activity has been shown to be of the binary type, since the active principle shows both activator type and plasmin type activity.
3. The resulting plasmin activation is insensitive to plasma antifibrinolytic agents, and in particular to $alpha_2$ antiplasmin.
4. No antigen effect.
5. High fibrin affinity.
6. No risk of hemorrhage within a wide dosage range, and thus excellent tolerance.
7. Exact measurement in units of fibrinolytic activity.

Table I below compares the therapeutic use of STK and UK on the one hand with that of angiokinase (AK) on the other.

TABLE I

| Streptokinase and Urokinase (STK) (UK) | Angiokinase (AK) |
|---|---|
| 1. Antibody inactivation (STK) | 1. No antibody inactivation |
| 2. Plasmatic antiplasmin inactivation | 2. No inactivation by plasmatic inhibitors |
| 3. Limited or scarce affinity for fibrin | 3. High affinity for fibrin |
| 4. Extraneous to blood coagulation homeostasis and to the relative fibrinolytic mechanism | 4. Legitimate part of blood coagulation homeostasis and the relative fibrinolytic mechanism |
| 5. Risk of hemorrhage | 5. No risk of hemorrhage |
| 6. Poor correspondence between dose and effect | 6. Good correspondence between dose and effect |
| 7. Activating action only | 7. Binary action: activating and plasmin |
| 8. Intravenous administration (phlebo- | 8. Intravenous, intramuscular and oral ad- |

TABLE I-continued

| Streptokinase and Urokinase (STK) (UK) | Angiokinase (AK) |
|---|---|
| clysis) | ministration |
| 9. Limited administration period | 9. Prolonged and repeated administration for any period of time |

It should be noted that the binary fibrinolytic action of angiokinase offers a considerable advantage in both absolute and relative (to STK and UK) terms: it allows fibrinolytic activity even in the deficit or absence of plasminogen, that is, in situations where an activator only is ineffective.

In turn, the lack of inhibition by plasmatic inhibitors guarantees a satisfactory correspondence and proportionality between dosage and the resulting effect.

Clearly, the discovery of the tissue (vascular) fibrinolytic active principle, that is of angiokinase, which is the object of the present invention represents important and real progress in the field of fibrinolytic and thrombolytic therapy. Said progress allows the use of the same fibrinolytic principle directly involved in coagulation homeostasis in the blood vessels.

SUMMARY OF THE INVENTION

Therefore, the object of the present invention is a process for the production of a vasal fibrinolytic active principle called angiokinase, starting from richly vascularized connective tissue from mammals, particularly the aorta of animals like cattle and pigs, where said process involves the following operations:

defatting, drying and pulverizing said tissue;

subjecting said powder to pancreatin lysis by forming an aqueous suspension of it at substantially neutral pH, adding approximately 1% by weight of pancreatin with respect to the weight of powder used, and by effecting pancreatin digestion at a temperature of 45°–50° C. for approximately 24 h with stirring, so as to prepare a lysate suspension;

acidifying the suspension to bring the lysate into solution and form a precipitate which is then removed from the solution by filtration;

neutralizing said solution and adding a sufficient quantity of ammonium sulfate to reach an ammonium sulfate concentration of approximately 35% of saturation, so as to precipitate said lysate;

collecting the precipitate containing the active principle and forming an aqueous suspension at neutral pH;

purifying said lysate suspension through selective fractionation operations which may be of several types, for example, through selective elution of a gel column followed by purification via selective fractionation via chromatography, or through elution using a large volume of gel in proportion to the liquid to be purified, leading to a dilute solution of the active principle which is then concentrated by removing some of the water; and collecting the fractions containing the angiokinase, checking the activity of said fractions in fibrinolysis.

Also an object of the present invention is the vasal fibrinolytic active principle called angiokinase, obtained via the procedure mentioned above, with a protein N content of 0.2 µg/ml and a mean molecular weight of about 18000 Dalton.

Another aspect of this invention is the application of angiokinase in human therapy for the prophylaxis and treatment of abnormal fibrin formation and of thrombus formation in its various manifestations.

The procedure for the preparation of the active principle is thus characterized by the choice of starting materials consisting of richly vascularized connective tissues to obtain a product containing the active principle in highly concentrated form, along with mainly proteinic impurities. Thus, successive purification is necessary to remove the undesired impurities.

BRIEF DESCRIPTION OF THE DRAWINGS

The detailed description below refers to the attached drawings, in which.

THE DETAILED DESCRIPTION OF THE INVENTION

Preparation Procedure

The starting material for the angiokinase extraction consists of various mammalian organs, particularly organs and connective tissue from cattle and pigs which have a high proportion of vascularized tissues.

According to the present invention, angiokinase was isolated and identified both from arterial and venal vasal tissue and from highly vascularized organs and tissues, in which it was present in quantities sufficient for extraction.

Examples of organs and tissues used for angiokinase extraction include the aorta, heart, lung, spleen, liver, pancreas, although the aorta is preferred, although the invention is not limited to these organs only.

The starting material is first treated to remove fats, for example by extraction with a solvent like acetone, and then dried, reduced to powder and subjected to pancreatin lysis. Lysis is performed by resuspending the dried organ in aqueous solution at neutral pH, for example in pH 7.4 phosphate buffer, and adding industrial pancreatin in a quantity equal to approximately 1% by weight with respect to the organ in suspension. Lysis is carried out by digestion at a temperature of 45°–50° C., preferably with constant stirring, for approximately 24 hours.

After the digestion, the insoluble portions are removed by centrifugation and the liquid is collected and acidified to pH 2.5, preferably with dilute HCl, until a precipitate is formed. The precipitate is again separated by centrifugation, and the liquid collected is neutralized to pH 7 by adding dilute NaOH.

The active component is separated from this neutralized liquid by adding ammonium sulfate ((NH$_4$)$_2$SO$_4$) until the concentration reaches 35% of total saturation. In this way a precipitate is formed which contains the active fibrinolytic component of the organ lysate.

The precipitate is collected by centrifugation and the liquid is discarded. The precipitate is then resuspended in a small volume of phosphate buffer at pH 7.4.

The resulting suspension is already a concentrated extract of the active principle angiokinase.

Various reproducible industrial methods may be used to effect this purification; the following two are cited as examples only.

The first method involves a two step purification: the first by gel filtration to give a partial purification and the second by fractionation via adsorption or ion exchange chromatography.

The second method consists of an operation analogous to the first step above, but with using higher ratios of gel to product to be purified so as to achieve greater purification in a single step. The resulting product is very dilute and requires successive concentration by removing the excess water.

In order to describe the invention in greater detail the following examples describe the operations carried out in purifying the lysate prepared as described above.

Example I First partial purification step of the lysate, using Sephadex G-25 filtration gel This is a simple and rapid method for the partial purification of large quantities of lysate prepared as described above, leading to good fractionation of the proteins based on their molecular weight. Along with other large molecules, the active principle is completely excluded by the gel and so is eluted immediately, while spherical globules below the highest fractionation limit (from 1000 to 5000 dalton, for the Sephadex G-25 used in this example) are eluted later.

This method also desalts the lysates, through combination with the buffer.

The advantage of this method is that it allows the filtration of large volumes: volumes of the substance to be eluted can be up to 30% of the volume of the gel. For example, approximately 300 ml of the organ lysate may be used for each liter of gel.

The following experimental conditions were used: 10 ml of bovine aorta lysate is placed on a column (2.6×40 cm) with Sephadex G-25 (60 ml gel, 33 ml/hour flow rate, approximately 5 ml every 9 minutes) in 0.1M TRIS buffer (trihydroxymethylaminomethane), treated with 0.02M CaCl$_2$ at pH 8.2.

The eluent is collected in 5 ml fractions. The fractions containing the active principle are checked by measuring their fibrinolysis activity, using the method described below. Under these experimental conditions, the active principles is eluted in the first eight fractions.

Figure 1:
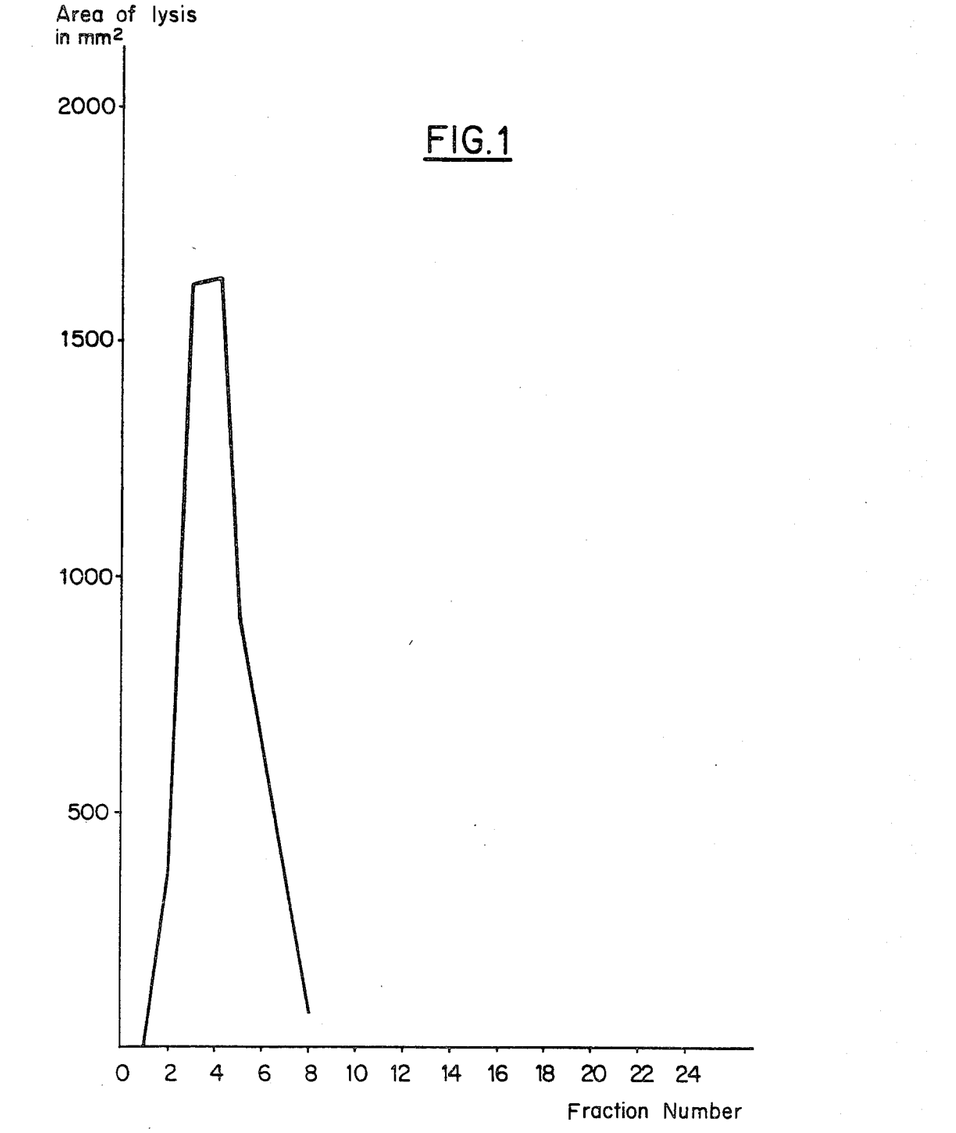
FIG. 1 is a diagram showing the fibrinolytic activity of the fractions obtained from the lysate during the first purification phase, using absorption chromatography.

FIG. 1 shows a graphical representation of the typical progress in this first partial purification of the organ lysate.

In FIG. 1, the fraction number is reported along the ordinate while the lysis area in mm$^2$ is reported along the abscissa (measured as described below).

Using the same methodology with a different buffer gives an analogous partial purification, for example using phosphate rather than TRIS buffer (again at pH 8.2), or 0.1M sodium acetate buffer (at another pH 45.0). These and other variations are well known to experts in this field. Before going on to the second step to achieve a high degree of purity of the active principle, a dialysis process must first be carried out. As mentioned above, after the first partial purification step, the angiokinase can be prepared using various purification methods. The following examples report only those with particularly advantageous results, although other methods may of course be used without going beyond the bounds of the present invention.

Example II Second step-total purification of angiokinase using adsorption chromatography The enzyme angiokinase can be purified via adsorption chromatography using various chromatographic substances, for example:

(A) Soy bean trypsin inhibitor (SBTI) bound to Sepharose (B) p-Aminobenzamidine (p-ABM) bound to Sepharose.

(II-A) Angiokinase purification by adsorption chromatography with soy bean trypsin inhibitor (SBTI) bound to Sepharose In adsorption chromatography, the substrate Sepharose (well known to be produced and sold worldwide by the Pharmacia Fine Chemicals Company, Uppsala, Sweden) bound here to SBTI, has affinity for the object of the present invention, angiokinase. This is due to the covalent bond formation between the activated substrate and the enzymatic protein, which is thus adsorbed from solution.

It is then de-sorbed by varying the pH, or ionic strength, of the medium, after the inert unbound material is eluted.

Preparation of SBTI-Sepharose 7.5 g of Sepharose 4B is washed on glass wool with a 0.001M NaCl solution (pH 8.3).

The washed gel is suspended in the above buffer, and stirred gently for approximately 2 hours at 4° C. Excess bonding agent is removed, by alternate washes with higher pH (0.1M TRIS+1.0M NaCl; pH 8.0) and lower pH (0.1M NaAcetate+1.0M NaCl; pH 4.0) buffers. At the end of the gel is obtained in the more acid buffer, ready for use.

Figure 2:
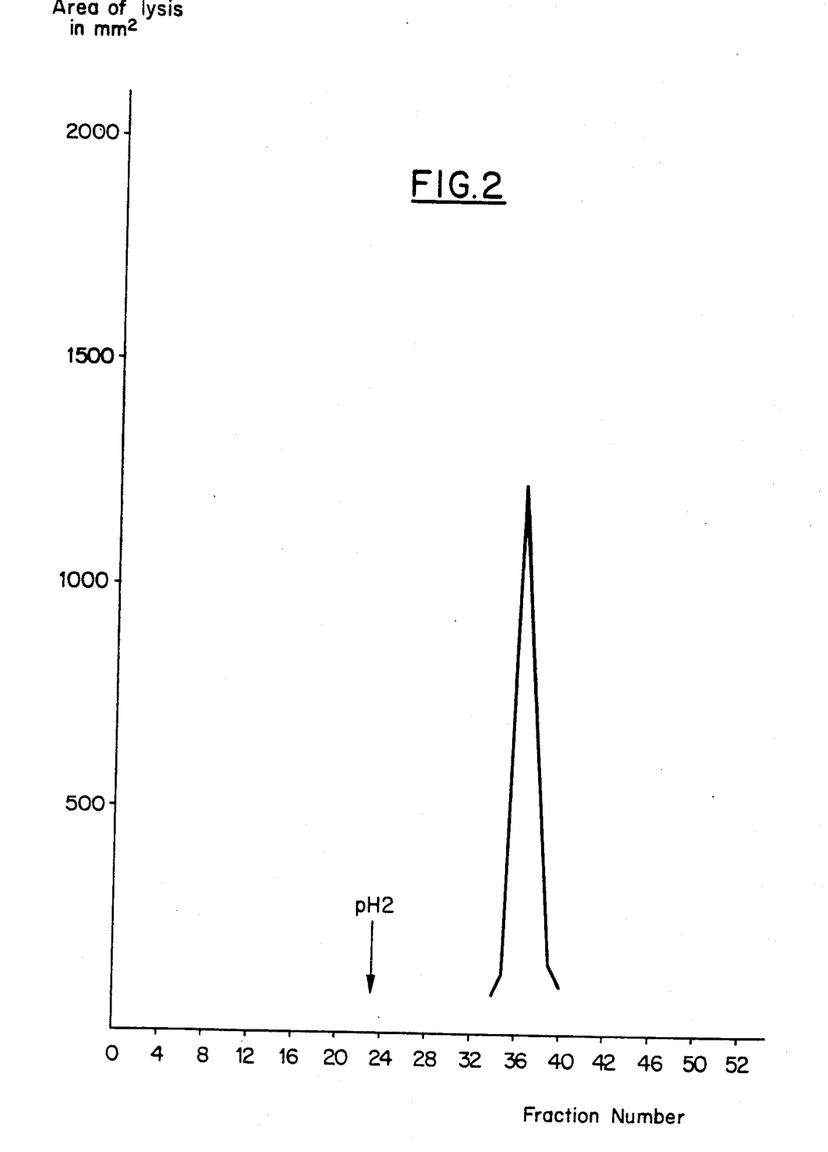
FIG. 2 is a diagram showing the fibrinolytic activity of the fractions obtained from the lysate during the second purification phase, using adsorption chromatography.

FIG. 2 gives a graphical representation of the adsorption chromatography of 10 ml of active bovine aorta lysate fractions (partially purified as described above with Sephadex G-25 in 0.1M TRIS+0.02M CaCl$_2$ buffer, pH 8.2). The fraction number is reported along the abscissa, while the lysis area in mm$^2$ is reported along the ordinate (measured as described below).

The progress of the adsorption chromatography was followed spectrophotometrically, at 280 nanometers in this case. The initial buffer was that mentioned above (pH 4.0). When the extinction coefficient at 280 nm reached 0, the buffer was replaced with one at pH 2.0 (0.2M KCl +0.2M HCl). The flow rate was approximately 3-5 ml/5 minutes. Every test tube collected was tested by UV.

As shown in FIG. 2, a sharp protein peak is obtained, coinciding with the onset of fibrinolytic activity, between the 40th and 48th fractions, corresponding to the isolation of angiokinase.

Angiokinase may also be purified starting directly from the organ lysate-without the partial purification described in example I. However, in thise case the lysate must be dialyzed with the same buffer.

(II-B) Angiokinase purification by adsorption chromatrography with p-aminobenzamide (p-ABM) bound to Sepharose The principle is as described above in example II-A.

Preparation of Sepharose with bound p-ABM 6 g of Sepharose 4B is weighed, and the gel is washed on a glass filter with 1000 ml of 0.5M NaCl (reagent A).

90 mg of N-ethyl-N'-(3-dimethyl-aminopropyl)-carbodiimide HCl is dissolved in 4 ml of distilled water and brought to pH 3.9 with 1 ml of 0.01M HCl (reagent B).

90 mg of p-aminobenzamidine is dissolved in 4 ml of distilled water at pH 4.5 (reagent C).

The three reagents (A,B,C) are mixed together to give a solution with final pH around 4.8 which is then stirred for 20 hours at room temperature. The resin is then washed with twice distilled water.

7 ml of Sepharose bonded to p-ABM is equilibrated with 4–5 volumes of 0.1M sodium phosphate at pH 7.6 in a 1 cm diameter column. The solution containing the angiokinase enzyme is then placed on the column (100 ml of partially purified organ lysate, brought to pH 7.6 with 0.1M TRIS buffer, are needed to saturate a column of 7 ml of Sepharose-p-ABM).

An aliquot of the lysate is kept aside to measure the activity.

Activity is measured before and after the partially purified lysate (example I) is passed through the bonded resin (measured by fibrinolysis or chromogenesis, as described below) to show when the column is saturated, i.e., when the activity is identical.

The column is then washed with 0.1M sodium phosphate buffer at pH 7.6 until the monitor shows 5% transmission, where the monitor is a continuously reading spectrophotometer set at 280 nanometers.

The column is then eluted with 0.1M benzamidine-HCl dissolved in the same buffer.

The samples to be colledted (4-5 ml) are those just after the optical density (O.D.) of the benzamidine effluent reaches the maximum value of approximately 90% absorbance.

The samples collected are dialyzed with 0.1M sodium phosphate buffer at pH 7.6 in a cold chamber at 4° C. with continuous stirring for 24 hours, with frequent changes. In this way, the benzamidine is removed and the dialyzed samples are frozen after the activity is measured (as described below).

Figure 3:
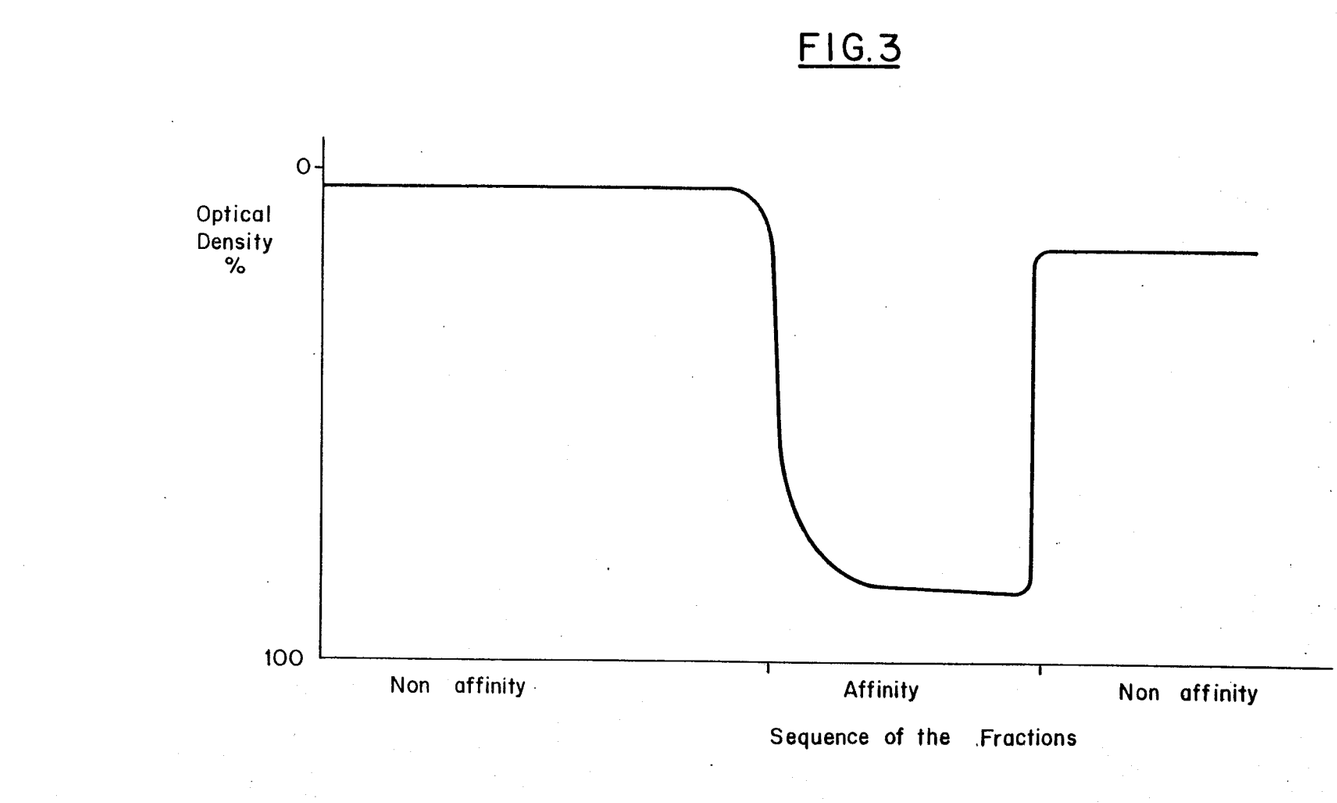
FIG. 3 is a spectrum used to check the adsorption chromatographic purification of the lysate.

FIG. 3 shows the spectrophotometric curve for the chromatography control, referring to the present example. % optical density is reported along the abscissa and fraction number along the ordinate.

Example III Second step-complete angiokinase purification using ion exchange chromatography In ion exchange chromatography, the gel contains negatively or positively charged groups. If the gel is positively charged (anion exchange), the negatively charged components of the solution to be purified are adsorbed. By using an eluent buffer of higher ionic strength, the proteins adsorbed are replaced by negative ions from the buffer (salt gradient). Each type of protein is selectively eluted at its specific gradient. This method allows complete purification of the angiokinase in the organ lysate treated as in example I;

Sephadex CM-50 (Pharmacia Fine Chemicals) has been found to be the ideal ion exchange resin for this purification.

The active fractions (from the 6th to 14th test tubes, for a total of 30 ml) of lysate partially purified by column chromatography on Sephadex G-25 (gel filtration as in example I) are combined and passed through a 24×188 mm column containing Sephadex CM-50 (60 ml) with 0.1M sodium acetate buffer at pH 5.0.

If the fractions of lysate partially purified on Sephadex G-25 are in pH 8.2 buffer, they must be dialyzed and taken up in pH 5.0 acetate buffer. This is not necessary if the partial purification of example I has been done directly at pH 5.0.

The flow is regulated to 16 ml/hour, and the fractions are collected with 5 ml/test tube. The progress of the chromatography is followed through continuous spectrophotometric reading at 280 nanometers as well as by measuring the fibrinolytic activity as described below.

The gradient is prepared by mixing 150 ml of 0.1M sodium acetate buffer with 150 ml of 0.1M sodium acetate+0.6M NaCl buffer.

Figure 4:
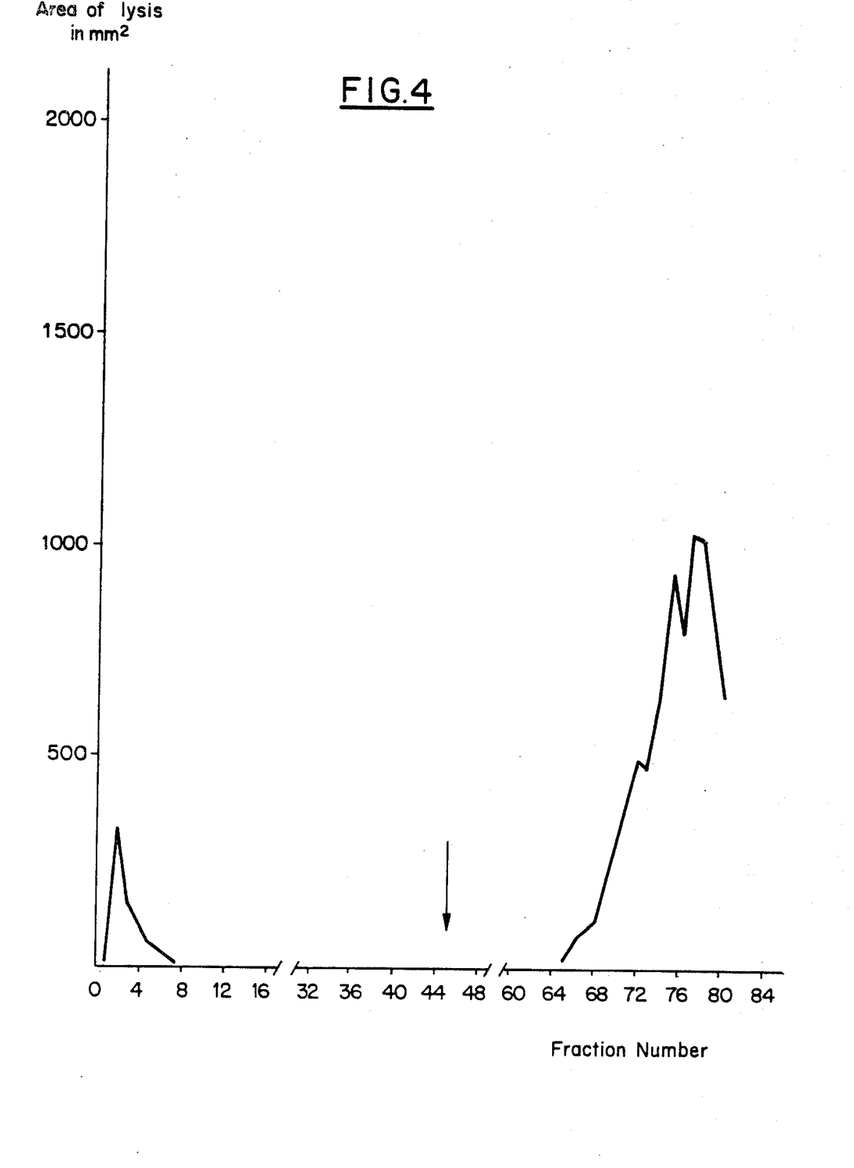
FIG. 4 shows the fibrinolytic activity of the fractions obtained from the lysate in the second purification phase using ion exchange chromatography.

FIG. 4 gives a graphical representation of angiokinase purification via ion exchange chromatography, as described in this example. Fraction number is reported along the ordinate, and lysis area in mm$^2$ along the abscissa.

The curve shows a first sharp peak corresponding to a low activity product. When the absorbance has returned to zero (from the 30th to 60th test tube), the molarity of the buffer is increased using the same sodium acetate buffer containing 0.6M NaCl (gradient application). In this way, ionic strength is increased, while the pH remains fixed at 5.0.

Under these conditions, other protein material passes (low peak, flat absorbance) corresponding to a high peak of activity. These are the fractions containing the purified angiokinase.

Example IV Complete angiokinase purification in a single step, using column chromatography with Sephadex G-25

This method is conceptually the same as that described in example I for the partial purification of the organ lysate from which angiokinase is extracted.

By varying the experimental conditions, that is by varying the ratio of gel volume to that of the substance to be chromatographed, the enzyme to be isolated may be purified even further. In other words, by greatly increasing the gel volume with respect to that in example I and by reducing the flow rate, the various fractions eluted may be partitioned more precisely to give fractions of angiokinase of a high degree of purity.

However, this operation must be followed by one in which these active fractions are concentrated, for example, via lyophilization, concentration at reduced pressure, and the like, since the enzyme is collected from the column in a highly dilute solution.

Properties of the product

Once the purified enzyme is prepared using the methods described above, it is then identified and characterized.

A preferred, but non-limiting, example of this process is a purified lysate from bovine arterial wall, prepared via pancreatin lysis according to this invention.

The following materials were used to evaluate the product, using the methods described below:

suine plasmin, activated with trypsin (Lysofibrin, Novo Laboratories, Copenhagen); 2 units of NOVO dissolved in 0.15M NaCl immediately before use;

human plasminogen, purified chromatographically from the plasma, supplied by the KABI Company, Stockholm, 15 U/mg specific activity;

human fibrinogen, prepared from Cohn fraction I, supplied by the KABI Company, Stockholm, dissolved in 0.1M TRIS buffer, pH 7.8;

thrombin (Topostasin, Roche, Basil), dissolved in 0.15M NaCl immediately before use;

Sephadex, CM-50, G-75 and G-100, supplied by the Pharmacia Fine Chemicals Company, Uppsala Sweden.

The results were compared with a previously known fibrinolytic agent;

Urokinase, supplied by the Leo Company, Copenhagen, in injectable form, in ampuls of 7100 CTA units each, dissolved in 0.15M NaCl immediately before use.

The following methods were used for data determination:

(1) Fibrinolytic activity was measured using Astrup and Müllertz' fibrin plate method, modified as described below (see 'Titration' section). Plasminogen-rich and plasminogen-free fibrin plates were used. The fibrinogen on the plasminogen-free plates was coagulated with plasminogen-free thrombin.

(2) The protein content was measured using the method of Lowry et al.

(3) Molecular weight was determined using 2.5×100 cm Sephadex G-100 columns, calibrated with Dertrane Blue (Vo) and $K_2CrO_4$ (Vt). Cytochrome C, ovoalbumin, bovine serum albumin and transferrin were used as controls.

(4) Electrophoresis on polyacrylamide gel: the sodium dodecylsulfate gel and buffers were prepared according to Weber and Osborn (1969) with and without beta-mercaptoethanol.

Acrylamide concentration in the gel was 10%. The gels were stained for proteins with Camassie Blue, or sliced into 1.0 mm thick disks with a slicer.

The disks were tested for fibrinolytic activity by placing them directly on the fibrin plates.

(5) Method for detecting possible plasminogen activation by the purified extract:

1.6 mg of plasminogen is dissolved in 2 ml of distilled water, and dialyzed for 12 hours with 0.01M sodium phosphate buffer (pH 7.0). A small quantity of undissolved material is removed by centrifugation at 4000 g at a temperature of $+4°$ C., for 20 minutes. The plasminogen solution is diluted with phosphate buffer to a final volume of 2 ml. 1 ml of purified extract (angiokinase, 0.025 extinction) is dialyzed analogously at the same time.

An ampul of urokinase is dissolved in phosphate buffer to the desired concentration.

The plasminogen is then incubated with the purified extract or urokinase in the following ratios:

0.3 ml plasminogen solution+0.1 ml angiokinase solution 0.3 ml plasminogen solution+0.1 ml urokinase solution 0.3 ml plasminogen solution+0.1 ml buffer.

The incubation period is two hours at $+37°$ C. The reaction is quenched by adding a small quantity of sodium dodecylsulfate and 2μ-liters of beta-mercaptoethanol in each test tube. 100μ liters of each of these solutions is then examined by electrophoresis on polyacrylamide gel.

Alternatively, the test solution may be incubated as follows:

0.3 ml plasminogen solution+0.1 ml glycerin+0.1 ml AK 0.3 ml plasminogen solution+0.1 ml glycerin+0.1 ml UK 0.3 ml plasminogen solution+0.1 ml glycerin+0.1 ml buffer.

The incubation period is 30 minutes, after the solution are examined as above.

Results

The following results were obtained from the measurements described above:

(1) The purified enzyme (angiokinase) is active on both the plasminogen-rich and plasminogen-free plates.

(2) The protein content of the purified enzyme (ion exchange) is $N=0.2$ μg/ml.

(3) The mean molecular weight of the angiokinase protein is approximately 18000 dalton.

(4) The electrophoresis results are consistent with those for direct fibrinolytic activity.

(5) Since both the starting extract and the purified principle were active on the fibrin plates both with and without plasminogen, the active principle was tested to determine whether it had plasmin activity only or a plasminogen activation effect as well. A preliminary test in which plasminogen was incubated in increasing concentrations in the presence of purified extract, showed that the fibrinolytic activity increases with the plasminogen concentration. This shows that angiokinase has a plasminogen activating effect.

The data from this experiment are reported in table II.

TABLE II

Angiokinase fibrinolytic activity as a function of plasminogen concentration

| Solutions | Fibrinolytic activity ($mm^2$ lysis) |
|---|---|
| 0.5 ml AK + 0.5 ml plasminogen 5.00 U/ml | 264.253 |
| 0.5 ml AK + 0.5 ml plasminogen 2.50 U/ml | 170.176 |
| 0.5 ml AK + 0.5 ml plasminogen 1.25 U/ml | 136.130 |
| 0.5 ml AK + 0.5 ml plasminogen 0.75 U/ml | 104.108 |
| 0.5 ml buffer + 0.5 ml plasminogen 5.00 U/ml | 22.22 |
| 0.5 ml buffer + 0.5 ml plasminogen 2.50 U/ml | trace |
| 0.5 ml buffer + 0.5 ml plasminogen 1.25 U/ml | 0.0 |
| 0.5 ml buffer + 0.5 ml plasminogne 0.75 U/ml | 0.0 |

K = angiokinase extract

As shown in the table, purified angiokinase shows increasing fibrinolytic activity as the plasminogen concentration increases. However, the same buffer with no angiokinase shows almost no activity, independent of the plasminogen concentration.

Angiokinase's plasminogen activation is confirmed by the polyacrylamide gel incubation and electrophoresis experiments described under 4.

Figure 5:
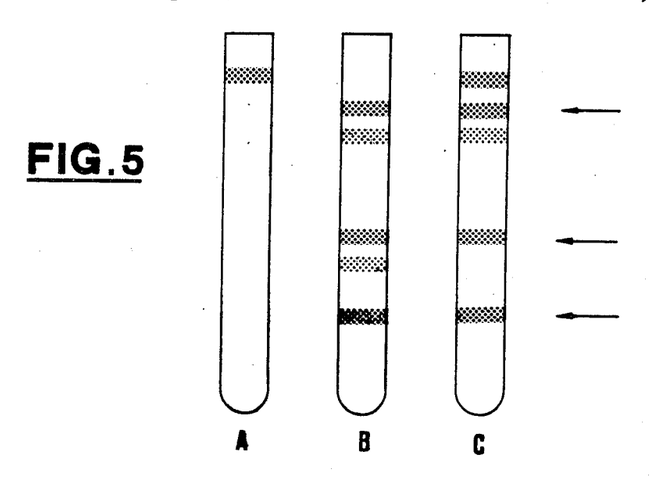
FIGS. 5 and 6 are diagrams representing angiokinase's plasminogen activation in experiments with short and long incubation periods, respectively.

FIG. 5 shows the results of the experiments on the plasminogen activating action of the purified extract, with short incubation periods and in the presence of 20% glycerine (7.5% polyacrylamide in the gel). In FIG. 5, gel A shows the plasminogen incubated with glycerine only. Under these conditions, there was no spontaneous activation; the plasminogen is present as a protein chain with a molecular weight around 90000 dalton. The changes in the molecule after incubation with urokinase are shown by gel B. Three molecular components (arrows) may be observed with molecular weights of 60000, 20000 and 10000 dalton. Gel C shows the changes in the plasminogen molecule after incubation with the purified extract according to the invention. There is a clear difference from gelA, with plasminogen only. In any case, a considerable portion of the plasminogen remained unchanged after incubation for 30 minutes.

Figure 6:
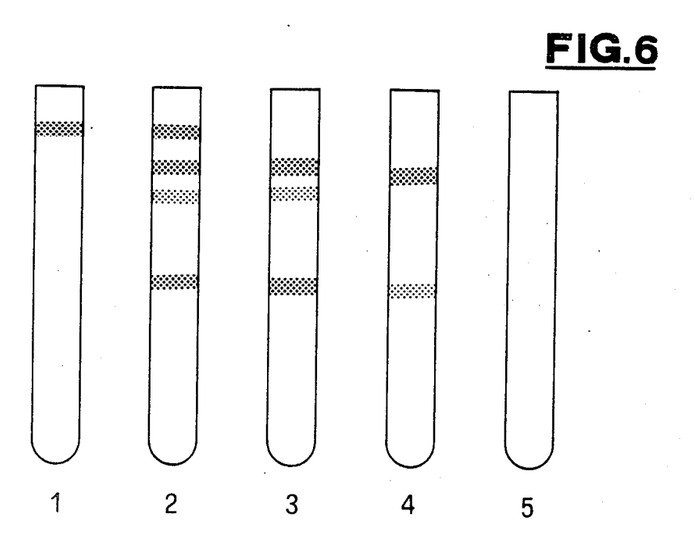

FIG. 6 reports the results of analogous experiments with long incubation periods. In this figure, gel 1 shows plasminogen incubated at 4° C. for two hours. Only the protein chain of the native plasminogen is visible.

Gel 2 shows plasminogen incubated for two hours at 37° C. The plasminogen was partially converted to plasmin. The three bands corresponding to molecular weights of 90000 (plasminogen), 60000 (heavy plasmin chains) and 20000 dalton (light plasmin chains) are visible.

Gel 3 corresponding to urokinase incubated with plasminogen under the same conditions shows complete activation. There are other bands showing autocatalytic activity on the part of the plasmin formed.

Gel 4 shows plasminogen incubated with the active principle according to this invention: the result is similar to that for urokinase, and activation is more complete than for gel 2 (plasminogen auto-activation). The protein quantities of urokinase and purified angiokinase extract were so small that they gave no band in the electrophoretic gel (gel 5).

These results show that the active principle of the angiokinase extract according to this invention attacks plasminogen with the formation of plasmin activity. While the molecular modifications induced are similar to those caused by urokinase, the reaction is slower. Plasminogen auto-activation occurs more rapidly in the presence of purified angiokinase extract.

The preceding description of the preparation procedure mentioned a method for measuring the fibrinolytic activity of the fractions extracted, as an index of the presence of angiokinase extract in the fraction.

The titration of the fibrinolytic substance isolated using the procedure above which is the object of the present invention is carried out as below, based on the fibrinolytic activity on fibrin plates.

Titration of purified angiokinase

Materials:
sterile plastic plates, inner diameter 93 mm;
human fibrinogen (Immuno) prepared with fractionation according to Cohn;
TRIS buffer, pH 7.8;
thrombin (Topostasin, Roche).
Method:
17 ml of a 0.1% human fibrinogen solution in pH 7.8 TRIS buffer is placed on the plate and coagulated with 0.04 ml of thrombin (15 NIHU/ml of physiological saline).

Under these conditions, a 2.5 mm thick film of fibrin is formed (2.503).

The activity of the isolated and purified angiokinase is measured by drawing 30μ liters with a precision pipet and placing it on the surface of the fibrin film to be incubated for 16 hours at 37° C. in a thermostat, while held perfectly horizontal.

A fibrinolytic unit (angiokinase unit, AU) is defined as the quantity of enzyme which causes a circular area of lysis 3.908 mm in diameter on plates of human fibrin, after 16 hours of incubation at 37° C.

This degree of lysis expressed as volume corresponds to the dissolution of a fibrin clot 0.1% in volume compared to the 30μ liters volume corresponding to the volume of purified angiokinase extract placed in contact with the fibrin.

Another widely known test is the euglobulin lysis time, which can be used to determine the concentration of modified angiokinase extract. Said euglobulin lysis time may be related to the AU value as defined for the preceding titration method.

Englobulin lysis time

Materials and methods

Male Wistar rats are used, weighing 200±5 g.

Blood samples were drawn from the open heart, under mild ether anesthesia, into silicon glass or plastic tubes.

3.8% sodium citrate was used as an anticoagulant in a 1:9 ratio to the blood. As soon as it was drawn, the blood was centrifuged at 2000 revolutions per minute for 15 minutes in a refrigerated centrifuge, so as to hold the temperature below +5° C.

The plasma so obtained was diluted with distilled water at +5° C. in the following ratio:
0.5 ml of plasma
9.0 ml of distilled water
0.1 ml of 1% acetic acid.

The mixture was held at +4° C. for 30 minutes, then centrifuged at 2000 revolutions per minute for 5 minutes in a refrigerated centrifuge. After the supernatant was removed, the residue was taken up in 1 ml of pH 7.8 phosphate buffer and placed in a thromboelastographic cuvette.

Triple Hartert-Hellige thromboelastograph cuvettes were used, in each of which 0.3 ml of englobulin solution was introduced using a high precision pipette. Exactly one minute later, coagulation was initiated with 0.06 ml of 1.29% calcium chloride. The piston was immediately lowered in each cuvette, and the coagulum was covered with a layer of liquid paraffin to being recording of the elastogram.

At the end of the curve, the lysis time is calculated along the longitudinal axis, from the point where the branches diverge 1 mm until the point where they converge 1 mm. This measurement is then converted to minutes based on the chart speed.

The animals were treated intraperitoneally 30 minutes before the intracardiac sampling.

The results of the test are reported below in table III, in proportion to the units of angiokinase.

TABLE III

| | Euglobulin lysis times per angiokinase unit | |
|---|---|---|
| | UA/kg bodyweight | Lysis time (minutes) | % activity |
| Controls | — | 85 | — |
| Angiokinase | 1,000 | 74 | 12.9 |
| " | 3,000 | 59 | 30.5 |
| " | 10,000 | 42 | 50.0 |

Pharmaceutical applications

On the basis of the results obtained, the present invention involves the use of the purified angiokinase extract, that is, of the angiokinase enzyme, in parenteral (for example, intravenous, intraarterial and intramuscular ampuls) and enteral pharmaceutical formulations (for example, gelatin capsules or tablets for oral administration). Of course, these examples do not limit the present invention in any way, since it extends to other possible pharmaceutical formulations and administration routes.

Clinical trials

Administration of angiokinase in human therapy has been shown to be free of local or systemic secondary effects. Given its excellent tolerance, angiokinase may also be given in loco, while the oral route should be used preferably for prevention or maintenance of results achieved via other routes.

Angiokinase is to be used clinically for the prevention and treatment of all conditions of abnormal fibrin formation and thrombus formation, in various sites and localizations. The following examples of its therapeutic indications are exemplifying only and do not limit the significance of the invention in any way.

Athero-arteriosclerosis at various levels (cerebral, coronary, peripheral) and related thrombosis phenomena (cerebral, coronary, peripheral).
Myocardial infarction.
Cerebral infarction.
Diabetic vasculopathies.
Arteriosclerotic and diabetic retinopathy; thrombosis of various retinas.
Venous thrombosis; thrombophlebitis.
Post-operatory thrombosis.
Thrombo-embolic disease; pulmonary embolism.

With regard to the various therapeutic dosages, the posology of angiokinase varies depending on the use (prophylactic or therapeutic) and the indications mentioned above, according to a general scheme exemplified as follows:

(A) Prophylaxis
From 10000 to 50000 AU daily, depending on the case.

(B) Atherosclerotic disease in its various localizations Diabetic retinopathy
From 50000 to 200000 AU daily, broken up into various doses during the day.

(C) Thrombosis and thromboembolisms in progress From 200000 to 1-2 milion AU daily, broken up into various doses during the day.

In cases listed in A and B above, treatment may be continued by the physician, without necessarily requiring blood coagulative control.

In cases listed in C, however, the treatment period should be limited, as a function of the progress in the individual case and the physician's opinion. Blood coagulation controls are recommended.

Example V Clinical trials with angiokinase 70 patients with athero-arteriosclerotic disease were treated: 26 cases of coronary, 18 of cerebral, 10 of retinal and 20 of peripheral (lower limbs). The treatment period was in general 30–35 consecutive days, and angiokinase (AK) was used in daily doses of 90000 AU.

Coronary vasculopathies:
Pronounced and often rapid attenuation of painful symptomatology was observed in a significant number of cases, involving stenocardiac pain and strain-induced dyspnea. Working capacity and physical exercise possibilities were clearly enhanced.

Of the objective symptomatology, a sharp reduction of arrythmia, up to its disappearance, was noted. Electrocardiograph modifications were observed leading to improved coronary irrigation (for example, attenuation or disappearance of S-T tract dyslevel and of extrasystolic phenomena).

In those cases where before treatment, stress tests led to the appearance or worsening of signs of coronary ischemia and arrythmia, treatment with AK led to a marked reduction or even disappearance of these phenomena.

Cerebral vasculopathies:
On the level of subjective symptomatology, the modifications observed were particularly significant both in degree and consistency.

A generally rapid improvement was noted in tone and mood, with marked attenuation or disappearance of the sense of disorientation, dizziness and headache, with improved memory and working capacity.

For the objective symptomatology, cases of recent or relatively recent motor deficit or sensitive disturbances showed a reduction or even complete disappearance of said manifestations, with a cause and effect relationship.

Ateriosclerotic retinopathy:
Examination of the ocular ground at the end of treatment showed pronounced improvement in the retina condition (more evident and complete in the most recent cases), with disappearance of the microthrombosis, absorption of exudates and renewal of visual acuity to a completely satisfactory level.

Peripheral vasculopathies:
Sharp regression, even up to complete disappearance, of the claudication was observed after the end of treatment. This complete disappearance was always observed in second stage cases.

Of the objective symptomatology, improved circulation in the affected areas was observed in a significant number of cases: more reasonable color and temperature returned to said area with noticeable improvement or regression of any trophic disturbances present (ulcerations, turbid sores), and at times with returned pulse in the pedal artery.

Example VI Laboratory and instrumental tests in the clinical trials

The following laboratory test results were obtained for the cases treated and observed in example V.

Cholesterol and lipid levels were affected only slightly in a non-significant way.

However, the blood coagulative area constantly showed a sharp and significant modification due to:

(a) the reduction or disappearance of the thrombophil condition, with usually unimportant lengthening of coagulation times;

(b) the normalization of the partial thromboplastic time;

(c) the considerable shortening of the lysis time (dilute blood lysis time, englobulin lysis time). Before treatment, these times were more or less noticeably lengthened. Treatment with AK brought them back to normal values, or at least shortened them.

In almost all cases where they were measured, the oscillograph results showed sharp improvement, even up to the point of normalization of the oscillation amplitude.

Acute thrombosis:
AK was also studied in cases of acute thrombosis attacks, that is, in ten cases of acute myocardial infarction, in 5 of cerebral thrombosis, and in 3 of peripheral thrombosis (femoral level).

Progress in all these cases of particular doctrinal and practical interest showed clearly the effective lysis activity, in terms of useful modifications in the blood coagulative area and in the clinical condition.

In these cases of acute thrombosis, the posology of AK was certainly higher than that used in example V:

from a minimum of 250000 AU to a maximum of 1000000 AU daily, depending on the case and its progress. AK was administered intravenously or by phleboclysis.

Acute myocardial infarction:

Pronounced and rapid improvement was noted in the clinical condition and pain symptomatology, with regression of the condition of collapse and rapid disappearance or marked reduction of arrythmia phenomena.

Progress in the cases treated was completely satisfactory, with significant and rapid modifications in the electrocardiograph condition, especially with regard to the S-T portion, the Q wave and the terminal T wave. More precisely, a regression in the dyslevel of the S-T portion was observed. This is well known to be an expression of lesion potential in the myocardial fibers in the perinfarcted area. Significant regressions were also observed in the characteristic alterations of the Q-R-S complex and in the negativity of the T wave.

On the level of enzymatic activity (transaminase, creatinphosphokinase), its rapid attenuation or disappearance was observed.

With regard to the clinical, instrumental and laboratory progress observed in these cases of acute myocardial infarction treated with AK, it should be emphasized that such progress is usually not observed with the therapies available prior to this invention.

Cerebral thrombosis:

In two cases, treatment with AK afforded a rapid return to normal conditions of motility and sensitivity in the affected hemisphere. Said return began 24–48 hours after the beginning of treatment, and developed within one week.

The other three cases showed a satisfactory although incomplete regression of the effects on the hemisphere involved.

Peripheral thrombosis, femoral thrombosis:

All three cases showed complete disappearance of the occlusion symptoms within 24–48 hours, with return to normal circulation in the ischemized areas, with returned pulse and oscillations.

It should be emphasized that none of the cases treated according to this invention showed any signs of hemorrhage, in the injection site or anywhere else. This includes the initially acute cases who received the highest dosage (1000000 AU daily).

Regular urinalysis revealed no hematuria. Tests of vasal fragility showed no pathological variations.

Therefore, based on the clinical and laboratory results for all the cases treated with angiokinase, even those at the highest dose, not only was a markedly antithrombophillic condition initiated, but a satisfactory condition of blood coagulative homeostasis was also maintained. No hemorrhagic situations were ever encountered.

These results, together with its undisputed antithrombotic activity, good manageability and therapeutic reliability, emphasize the usefulness of the new substance angiokinase, according to this invention, as compared with other previously known therapies.

By the very nature of the invention, the comparison can only be indirect, leaving to each practitioner to decide on a case-by-case basis whether to apply the treatment covered by this invention rather than previously known ones.

We claim:

1. Process for the production of a vasal fibrinolytic active principle called angiokinase enzyme, starting from richly vascularized mammalian connective tissue, said process comprising defatting, drying and pulverizing said tissue to a powder; subjecting said powder to pancreatin lysis by forming an aqueous suspension of it at substantially neutral pH, adding approximately 1% by weight of pancreatin with respect to the weight of powder used, maintaining a temperature of 45° to 50° for approximately 24 hours, so as to prepare a lysate;

acidifying the lysate with diluted mineral acid, separating liquid from the resulting precipitate and reneutralizing said liquid;

adding a sufficient quantity of ammonium sulfate to the reneutralized liquid to reach an ammonium sulfate concentration of approximately 35% of saturation, so as to precipitate the active part of the lysate;

collecting the precipitate and forming an aqueous suspension of it at neutral pH;

purifying said lysate suspension through selective fractionation operations consisting of adsorption operations; collecting the fractions containing angiokinase, as selected by measuring fibrinolysis activity both in the presence and absence of plasminogen, where said fibrinolytic activity is such that 30 $\mu$liters of angiokinase extract form a circular lysis area 3.908 mm in diameter on plates of human fibrin 2.503 mm thick, after 16 hours incubation at 37° C., wherein said product has a protein N content of 0.2 $\mu$g/ml and a mean molecular weight of about 18000 dalton.

2. Process according to claim 1, wherein said defatting is effected through extraction of the fats with acetone as solvent.

3. Process according to claim 1, wherein a pH of 7.4 is maintained in the pancreatin lysis operation using phosphate buffer.

4. Process according to claim 1, wherein said pancreatin lysis is effected with constant stirring.

5. Process according to claim 1, wherin said acidification of the lysate is effected by adding HCl to a pH of 2.5.

6. Process according to claim 1, wherein the liquid obtained in the acidification operation is neutralized by adding dilute NaOH.

7. Process according to claim 1, wherein said lysate purification operation includes a first step of partial purification involving a fractionation of the proteins based on their molecular weight via selective elution from a gel column, followed by a second purification step involving selective fractionation via chromatography.

8. Process according to claim 7, wherein said second step involves selective fractionation based on adsorption chromatography using chromatographic substances.

9. Process according to claim 8, wherein said chromatographic substance is a soy bean trypsin inhibitor.

10. Process according to claim 9, wherein said chromatographic substance is p-aminobenzamidine.

11. Process according to claim 7, wherein said second step involves a selective fractionation operation via ion exchange chromatography.

12. Process according to claim 1, wherein said lysate purification operation involves selective elution of the lysate on a gel column, with a relatively high ratio of gel volume to impure lysate volume, followed by concentration by removing part of the excess water.

13. Process according to claim 1, wherein said connective tissues are selected from arterial or venal vasal tissues, heart, lung, spleen, liver, and pancreas from cattle and pigs.

14. Process according to claim 13, wherein said vasal tissues consist of the aorta.

15. Vasal fibrinolytic active principle obtained with a process as claimed in claim 1.

16. Vasal fibrinolytic active principle which may be known chemically as angiokinase enzyme, wherein said principle is isolated as a chemical species by extraction of vascular and richly vascularized connective tissues from mammals, through enzymatic lysis, and has a protein N level of 0.2 µg/ml as measured with Lowry's method, as well as a mean molecular weight of approximately 18000 dalton; said principle has a fibrinolytic effect on fibrin both in the presence and absence of plasminogen, where said fibrinolytic activity is such that 30 µliters of angiokinase extract form a circular lysis area 3.908 mm in diameter on plates of human fibrin 2.503 mm thick, after 16 hours incubation at 37° C.

17. Active principle according to claim 16, wherein said enzymatic lysis is pancreatin lysis.

18. Active principle according to claim 16, wherein said mammalian connective tissues are arterial or venal vasal tissues, heart, lung, spleen, liver, and pancreas from cattle and pigs.

19. Active principle according to claim 18, wherein said vasal tissues consist of the aorta.

* * * * *